United States Patent [19]
Bonnet et al.

[11] Patent Number: 6,149,601
[45] Date of Patent: Nov. 21, 2000

[54] DETERMINING THE RHYTHM OF THE SPONTANEOUS DEPOLARIZATION OF THE MYOCARDIUM

[75] Inventors: Jean-Luc Bonnet, Montrouge; Remi Nitzsche, Gambais, both of France

[73] Assignee: ELA Medical S.A., Montrouge, France

[21] Appl. No.: 09/166,804

[22] Filed: Oct. 6, 1998

[30] Foreign Application Priority Data

Oct. 7, 1997 [FR] France .................................. 97 12463

[51] Int. Cl.$^7$ ................................................. A61N 5/0402
[52] U.S. Cl. ......................................................... 600/510
[58] Field of Search ................................. 600/510; 607/27

[56] References Cited

U.S. PATENT DOCUMENTS 5,273,049  12/1993  Steinhaus et al. .

FOREIGN PATENT DOCUMENTS 0 321 764  6/1989  European Pat. Off. .
0 554 208  8/1993  European Pat. Off. .

OTHER PUBLICATIONS

Edward V. Simpson et al., "*An Automatic Activation Detector for Bipolar Cardiac Electrograms*", Cardiology and Imaging, New Orleans, LA, Nov. 4–7, 1988, pp. 113–114.

M. Kirhner et al., "*Real–Time Interval Measruement During Invasive Cardiac Electrophysiologic Testing*", Proceedings of the Computers In cardiology Meeting, Leuven, Belgium, Sep. 12–15, 1987, pp. 93–96.

*Primary Examiner*—William E. Kamm
*Attorney, Agent, or Firm*—Orrick, Herrington & Sutcliffe, LLP

[57] ABSTRACT

An active implantable medical device, particularly a cardiac pacemaker, defibrillator and/or cardiovertor capable of detecting the spontaneous depolarisation of the myocardium and determining the instant of its occurrence, which device detects the spontaneous depolarisation (10) of the myocardium through processing of a cardiac signal (E), delivers an information (t) of occurrence of a depolarisation and conditionally discriminates, preferably during consecutive limited time intervals ([t−50, t+200]), a unique characteristic of the cardiac signal giving a temporal information ($T_1$, $T_2$, $T_3$) on the instant of occurrence of the depolarisation. The unique characteristic can particularly be a predetermined singularity of the cardiac signal such as an extreme, particularly the extreme negative, of the first derivative (dE/dt) of the cardiac signal.

9 Claims, 4 Drawing Sheets

FIG_3

DETERMINING THE RHYTHM OF THE SPONTANEOUS DEPOLARIZATION OF THE MYOCARDIUM

FIELD OF THE INVENTION

This invention relates to active implantable medical devices such as those defined in the Jun. 20, 1990 Directive 90/385/EEC of the European Community Council, and more particularly, to active implantable medical devices like cardiac pacemakers, defibrillators and/or cardiovertors that include a function of detecting the spontaneous depolarisation of the myocardium.

BACKGROUND OF THE INVENTION

Active implantable medical devices such as those defined in directive 90/385/EEC of Jun. 20, 1990 of the European Community Council are known to analyse different signals emitted by the myocardium, which signals are composed of different waves, to detect the spontaneous depolarisation of the myocardium. Such devices include cardiac pacemakers, defibrillators and/or cardiovertors. Detection of a depolarisation wave in these signals is revealing of spontaneous myocardial cell activity, either in the atrial cavity or the ventricular cavity, and is necessary for the various functions of these devices.

The detection of such a depolarisation wave allows, first of all, to reset various temporal (i.e., timing related) commands of the device, such as an escape-interval, or, to release (i.e., trigger) some other function, such as an atrio-ventricular delay.

This detection is also used to command the functioning of certain algorithms conventionally implemented in the implanted device, such as algorithms of fallback, rate smoothing, etc. The detection of the spontaneous ventricular rhythm, particularly the analysis of its stability, is also, in some implantable defibrillators, an essential parameter for the appropriate release of a shock therapy.

Finally, some devices are equipped with "Holter" memory functions allowing for continuous monitoring of parameters of the cardiac rhythm, especially for evaluating the stability of the rhythm for diagnostic and/or therapeutic purposes.

Systems for the detection of depolarisation waves are known and they use various means. One such system is described in EP-A-0 605 264 and its corresponding U.S. Pat. No. 5,388,586, commonly owned by the assignee of this application Ela Medical, which uses a filtering of the myocardial signal in a selected frequency range, for example 30 to 80 Hz, where the filtered signal is then applied to a threshold circuit, with unilateral or bilateral threshold, for detection of the depolarisation wave.

More elaborate systems are also known, for example, the system discussed in EP-A-0775 502 and its corresponding U.S. patent application Ser. No. 08/755,335, now U.S. Pat. No. 5,836,980 also commonly owned by Ela Medical, where detection is based on an analysis of the first derivative (rate of increase) of the signal.

In all cases, the detection of the presence of a depolarisation wave in the most rapid and reliable (with regard to sensitivity) manner possible is desired. Indeed, the rapidity of detection is important because the presence of a possible spontaneous depolarisation wave must be signalled before the end of the relevant escape interval, otherwise stimulation could be applied unnecessarily.

Although not harmful, it is desirable to avoid such a stimulation simultaneous to spontaneous activity (a phenomenon known as "fusion"), on the one hand to save energy, and on the other hand, so that the spontaneous activity of the patient can be monitored by the system without the presence of such extraneous signals (i.e., the stimulation), for example, for diagnostic functions or for algorithms which are able to predict arrhythmia based on the stability of the spontaneous rhythm.

Known detection processes suitably meet sensitivity and rapidity requirements in the detection of the presence of a spontaneous depolarisation wave. Nevertheless, they suffer the disadvantage of not always indicating, from one cycle to the next, the same instant at which the depolarisation wave is detected.

As the depolarisation wave comprises several phases that may vary slightly from one cycle to another and one can find in some cycles, a slight modification or variation of amplitude, or even morphology, prior art detection systems can only detect alternately one phase of the wave or another (for example, a positive peak or a negative peak). As a result, a stable rhythm (in regard of the different components of the signal) will appear unstable to those systems, with variations which are typically greater than 20 ms.

This presents a notable disadvantage precisely when the objective is to measure temporal parameters of the rhythm, for example, for purposes of diagnosis or to determine the behaviour of certain algorithms.

OBJECTS AND SUMMARY OF THE INVENTION

Among the objects of the present invention is to provide a device and method for depolarisation detection that is both rapid—i.e., capable of rapid delivery of information of the occurrence or non occurrence of a depolarisation (a qualitative aspect)—and sensitive—i.e., capable of providing sufficiently specific temporal definition of the instant of the occurrence of the depolarisation (a quantitative aspect, allowing the measure of the temporal sequence of waves of a similar nature, which are always seen on the same component of the wave by the system).

Accordingly, times measured by detection according to the present invention (for example, delay between successive depolarisation waves) will correspond to the true characteristics of the rhythm.

To this end, detection of the spontaneous depolarisation of the myocardium in a device according to the present invention comprises first means of processing a cardiac signal for detecting and delivering information of the occurrence of a depolarisation, and secondary processing means of the cardiac signal for discriminating a unique characteristic of the cardiac signal giving temporal information as to the instant of occurrence of the depolarisation, the secondary means being implemented conditionally during the same cardiac cycle in the case of an occurrence of depolarisation detected by the first means.

In one implementation, the secondary means comprises means for discriminating a peak of auto-correlation in the cardiac signal, the instant of occurrence of the depolarisation being deduced from the temporal position of this peak.

In an alternative implementation, the unique characteristic is a predetermined singularity of the cardiac signal, the temporal position of this singularity defining the instant of occurrence of the depolarisation. This singularity can be an extreme (particularly the negative extreme), the first derivative of the cardiac signal, or the maximum of amplitude of the cardiac signal.

The secondary processing means of the cardiac signal is advantageously implemented during a limited time interval, either beginning at or before the instant where the occurrence of the depolarisation is detected by the first means.

The first means can be a means of detection of the crossing of an amplitude threshold by the cardiac signal.

A method of detection of the spontaneous depolarisation of the myocardium according to the present invention comprises the steps of processing a cardiac signal for detecting and delivering information of occurrence of a depolarisation and discriminating a unique characteristic of the cardiac signal giving temporal information as to the instant of occurrence of the depolarisation, the discrimination implemented conditionally during the same cardiac cycle in the case of an occurrence of depolarisation detected by the first means.

In one implementation, the discrimination is implemented by discriminating a peak of auto-correlation in the cardiac signal, the instant of occurrence of the depolarisation being deduced from the temporal position of this peak.

In an alternative implementation, the unique characteristic is a predetermined singularity of the cardiac signal, the temporal position of this singularity defining the instant of occurrence of the depolarisation. This singularity can be an extreme (particularly the negative extreme), the first derivative of the cardiac signal, or the maximum of amplitude of the cardiac signal.

Discrimination is advantageously implemented during a limited time interval, either beginning at or before the instant where the occurrence of the depolarisation is detected by the first means.

Detection of the spontaneous depolarisation can alternatively be based on the crossing of an amplitude threshold by the cardiac signal.

BRIEF DESCRIPTION OF THE DRAWINGS

Further features, characteristics and advantages of the invention will be evident to those persons of ordinary skill in the art in view of the following detailed description of a preferred embodiment of the present invention, made with reference to the annexed drawings, in which.

DETAILED DESCRIPTION OF THE DRAWINGS

Figure 1:
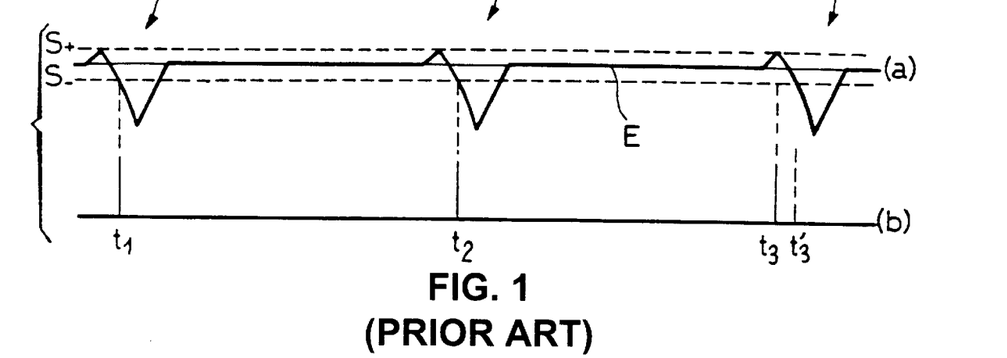
FIG. 1 illustrates a prior art depolarisation detection by a known spontaneous depolarisation detection system.

In FIG. 1, three successive cycles 10, 12, 14 of endocardial signal E are illustrated, resulting from a spontaneous depolarisation of the myocardium.

Prior art detection systems generally use an amplitude threshold technique wherein, when the amplitude of the endocardial signal E exceeds, in absolute value, a predetermined threshold S (S+ or S−), a spontaneous depolarisation of the myocardium is detected. Of course, the present invention is applicable to any system suitable for detecting spontaneous depolarisation and is not limited to the described system.

If endocardial signal E has some irregularities from one wave to the next, as is sometimes the case, inconsistent results can be obtained. For example, for waves 10 and 12 the crossing of the threshold takes place on the negative threshold S− whereas for wave 14, where the amplitude of the precursor of the wave is slightly larger than that of the two preceding waves 10 and 12, the detection occurs on the positive threshold S+. For wave 14, the detection will occur at instant $t_3$ (i.e., the crossing of threshold S+) before the instant $t'_3$, instant $t'_3$ being the equivalent of instants $t_1$ and $t_2$ (that is to say the instant where crossing of the negative threshold S− occurs) for waves 10 and 12 where wave 14 would have crossed the threshold had it been of the same amplitude as waves 10 and 12.

Thus for the illustrative waves, detection of a depolarisation is deemed at threshold crossing instants $t_1$, $t_2$ and $t_3$ on FIG. 1.

The points of detection at instants $t_1$, $t_2$ and $t_3$, firstly, reveal occurrence of a spontaneous depolarisation and secondly, allow evaluation of duration intervals $I_1=t_2-t_1$, $I_2=t_3-t_2$, etc., representative of the intervals separating two successive depolarisations (intervals R—R).

While there is no false detection caused by the irregularity of wave 14 (with respect to waves 10 and 12), rather only an anticipated or premature detection, this can nonetheless have a negative impact on the evaluation of the stability of the rhythm because, even in the presence of a stable rhythm (as in the case of the FIG. 1), the system will determine a calculated interval $I_2=t_3-t_2$ that is shorter than the real (equivalent) interval $t'_3-t_2$. One observes as well that prior art detection systems can from time to time present anomalies in the calculation of the interval R—R, and therefore, in the evaluation of the variability of the rhythm over several successive cycles, anomalies not corresponding to a real variability of the rhythm.

In others words, even in the presence of a stable rhythm, the prior art system can detect, wrongly, an instability of this rhythm, due in fact to the variability of the instant of detection of the wave of depolarisation from one cycle to the next, and not to a variation of the periodicity of the waves themselves.

One could indeed mitigate this disadvantage by increasing the threshold S, but this would be to the detriment of the rapidity of the system response. This would be a major disadvantage because it is necessary to determine in the most advanced manner possible (i.e., as early as possible) if a depolarisation wave has or has not occurred, so that necessary measures can be taken, particularly to avoid the release of an inopportune stimulation.

Additionally, such an elevation of the threshold would be prejudicial to the quality of the detection (i.e., with respect to sensitivity), mainly in the case of arrhythmia.

Figure 2:
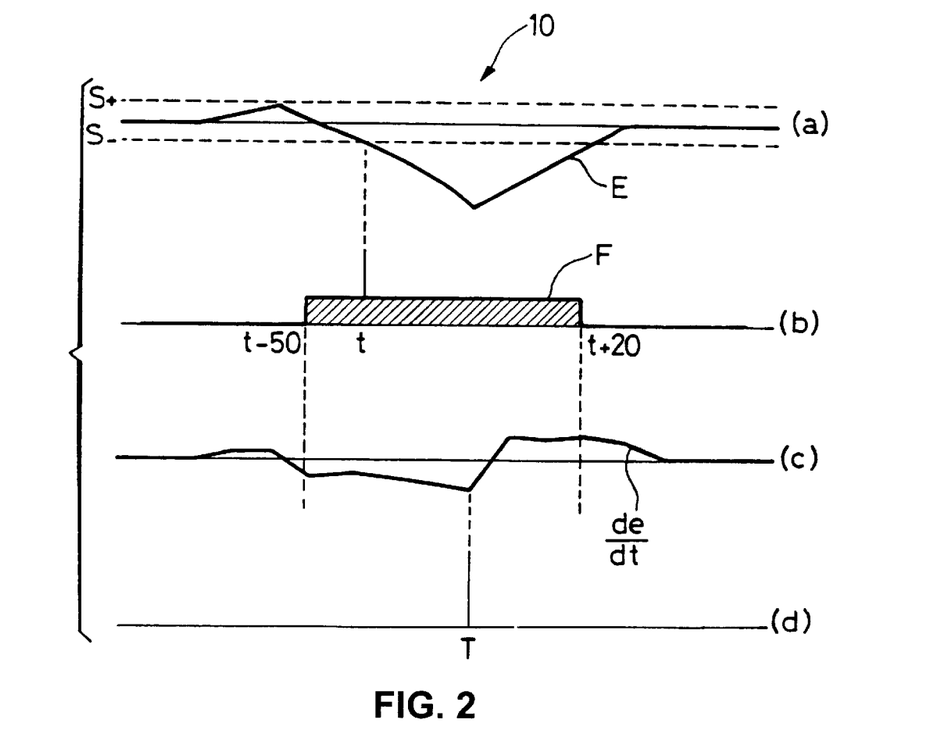
FIG. 2 illustrates a depolarisation detection by a system according to a preferred embodiment of the present invention.

FIG. 2 illustrates detection of depolarisation according to the present invention, which is designed to overcome the foregoing disadvantages.

A fundamental aspect of the present invention is the operational cascading of two distinct detection systems.

In a preferred embodiment, the first of the two systems is a classic system, either threshold or analog (for example, the system disclosed in the aforementioned EP-A-0 775 502 and U.S. patent application Ser. No. 08/755,335 based on the analysis of the first derivative of the signal, which disclosure is incorporated herein by reference), as described with reference to the FIG. 1 and illustrated on diagram (a) in FIG. 2, that presents the advantage of allowing sensitive and rapid detection of the occurrence of a spontaneous depolarisation, at instant t on diagram (b) of the FIG. 2.

The first system is not used for the measure of intervals between cycles. This parameter is evaluated by the second, less rapid but more specific, system of detection.

The two systems do not (operationally) work in parallel, but in cascade, as a mechanism with double onset—this is to say, the second system (for the evaluation of the interval of the cycle) is activated during the same cardiac cycle only if the first system (detection of a spontaneous depolarisation) has revealed the occurrence of a first depolarisation and does not indicate the detection of a following one.

At this moment, the second system opens a "window of analysis", for example, a limited time interval on the order of 200 ms, while it discriminates a predetermined singularity within the endocardial signal, the temporal position of this singularity defining the instant of occurrence of the depolarisation for evaluation of the variability of the rhythm. It is also possible to provide a supplementary retrograde window of, for example, −50 ms: the total consequent window being [−50 ms, +200 ms] around the primary detection t, as illustrated on diagram (b) of FIG. 2.

The singularity in question can be particularly the negative extreme of the first derivative of the cardiac signal. As illustrated on diagram (c) of FIG. 2, the derivative dE/dt of endocardial signal E (in practice, endocardial signal E is the signal given by successive increments ΔE of the cardiac signal sampled by discrete intervals Δt of the sampling frequency) presents a maximal absolute value at instant T (diagram (d)).

The choice of this particular singularity presents the advantage of being a unique criterion for a given wave. For cycles of a similar nature, this criterion will not be influenced by modifications or variations in the signal such as of the amplitude or the variability of the base line.

Figure 3:
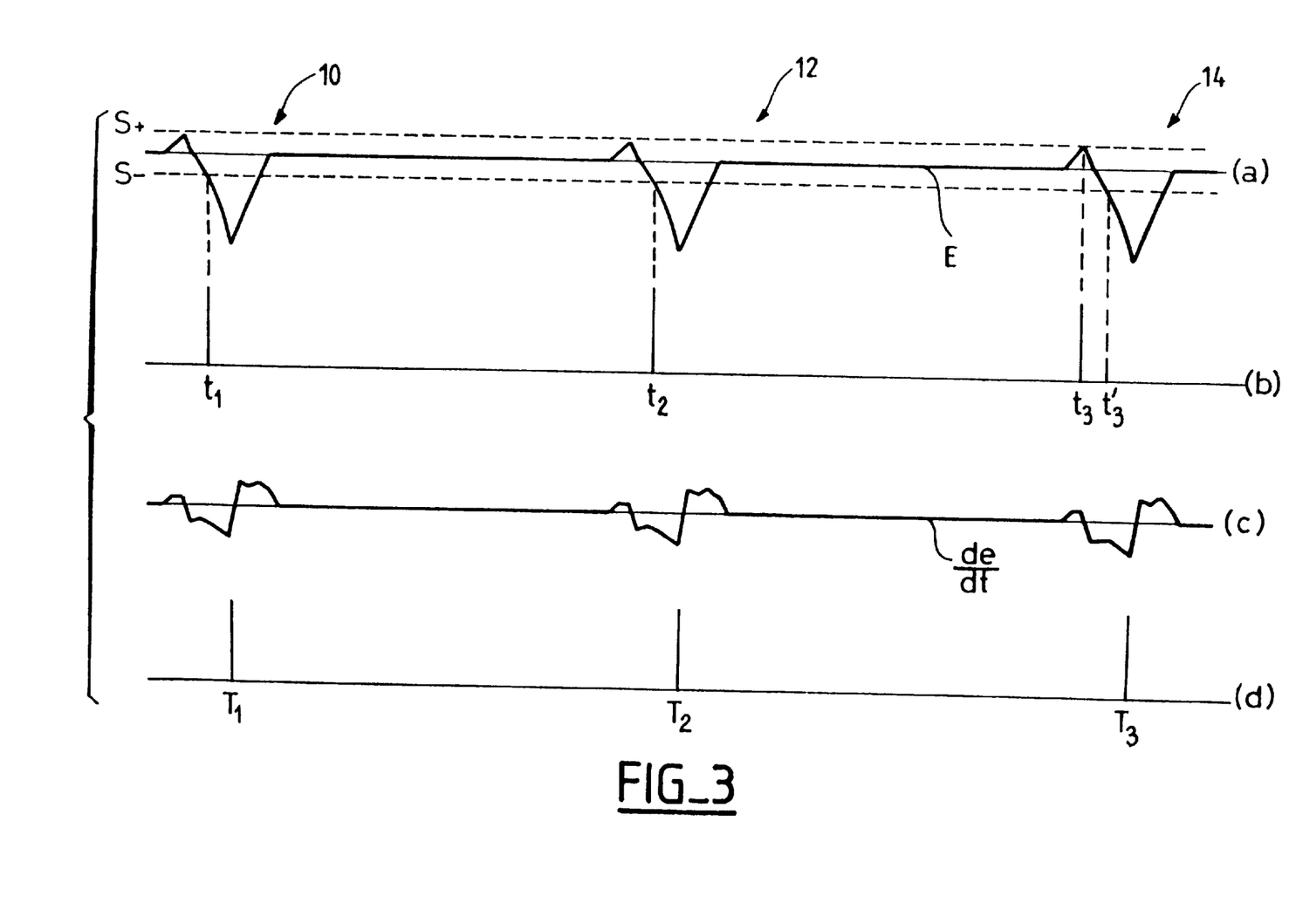
FIG. 3 is a comparative display between the prior art system of FIG. 1 and the system according to the present invention of FIG. 2.

FIG. 3 illustrates in comparative form the advantages obtained in accordance with the present invention.

Diagrams (a) and (b) in FIG. 3 correspond to diagrams (a) and (b) of FIG. 1, and (c) and (d) of FIG. 3 to (c) and (d) of FIG. 2, for three successive cardiac cycles.

As one can observe, even if the form of the wave varies slightly from one cycle to the next, intervals $I'_1=T_2-T_1$, $I'_2=T_3-T_2$, etc. (diagram (d)) will present excellent stability charactersistics compared to intervals $I_1=t_2-t_1$, $I_2=t_3-t_2$, etc. (diagram (b)) evaluated by threshold systems of the prior art. With implementation of the present invention, the measured instability will therefore be intrinsic to the rhythm, and no longer due to the system of measure.

The detection system of the present invention will therefore provide for each detected depolarisation wave, two pieces of information, namely:

a point of detection, at instant t (diagram (b) FIG. 2), informing the pacemaker in a sensitive and rapid manner that a spontaneous depolarisation has occurred; and a point of synchronisation, at instant T (diagram (d) FIG. 2), delivered secondarily but in a more specific manner, for purposes of measuring temporal sequences between the different waves of cardiac activity.

The maximum of the first derivative of the signal is not the only singularity that one can choose. One can, for example, choose one extreme of the endocardial signal, or again the crossing of a threshold S' (S'>S), without departing from the principle of the present invention.

As will be understood, in the present invention, it is not the absolute temporal positions of instant $T_1$, $T_2$, $T_3$ that is determinative, but their relative temporal position from one cycle to the next. It is important to have a signal presenting the maximum of specificity, that is to say a signal the most representative possible of the successive wave periodicity, and it matters little whether this signal is obtained in an anticipatory or premature manner or not inside a given cycle.

In another implementation, one can envisage discriminating the unique characteristic in the cardiac signal by a method of auto-correlation. In such a method, the system records during the window of analysis of the cardiac signal at high frequency. During the next detection by the first means, the cardiac signal is recorded in the same manner. Discrimination of the peak of auto-correlation between information contained in the two windows of analysis allows one then to determine the moment T where the depolarisation in the sense of the present invention has occurred.

The gap in the superposition of windows gives the gap of the third cardiac cycle of FIGS. 1 and 2 ($t'_3-t_3$).

Figure 4:
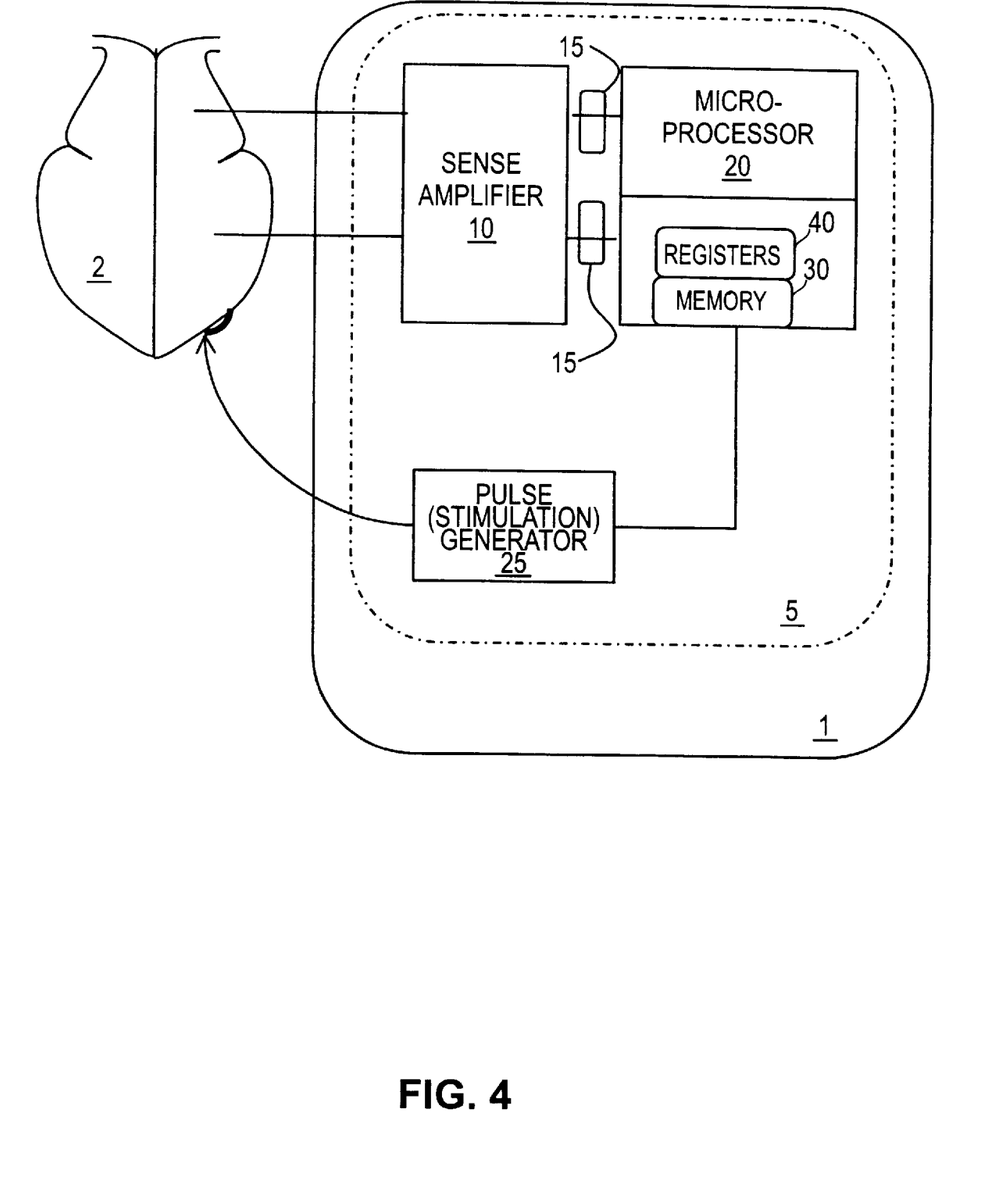
FIG. 4 is a block circuit representation of one embodiment of an active implantable medical device according to the present invention.

Referring now to FIG. 4, an active implantable medical device 1 of the cardiac pacemaker of defibrillator/cardiovertor type is shown with conventional electronic means 5 for performing the necessary functions for detection of spontaneous depolarisation of the myocardium according to the present invention.

Electronic means 5 includes, for example, digital microprocessor 20 controlled devices having sense amplifier 10, analog-to-digital conversion circuitry 15, memory 30 and registers 40 for data processing and manipulation and pulse (stimulation) generator 25. Such devices are commercially known, for example, in the CHORUS™ and TALENT™ series of products available from the assignee hereof, Ela Medical.

The present invention is preferably implemented under software control, and occurs in conjunction with acquisition of appropriate electric signals indicative of cardiac activity by conventional sense amplifiers, preferably after the acquired signals have been conditioned and converted to digital form in a known or conventional manner. Accordingly, programmable parameters, such as predetermined criteria and threshold values, are useful in implementation of the method of the present invention.

The method may also be performed using discrete digital logic, or analog circuitry without departing from the scope of the invention.

Figure 5:
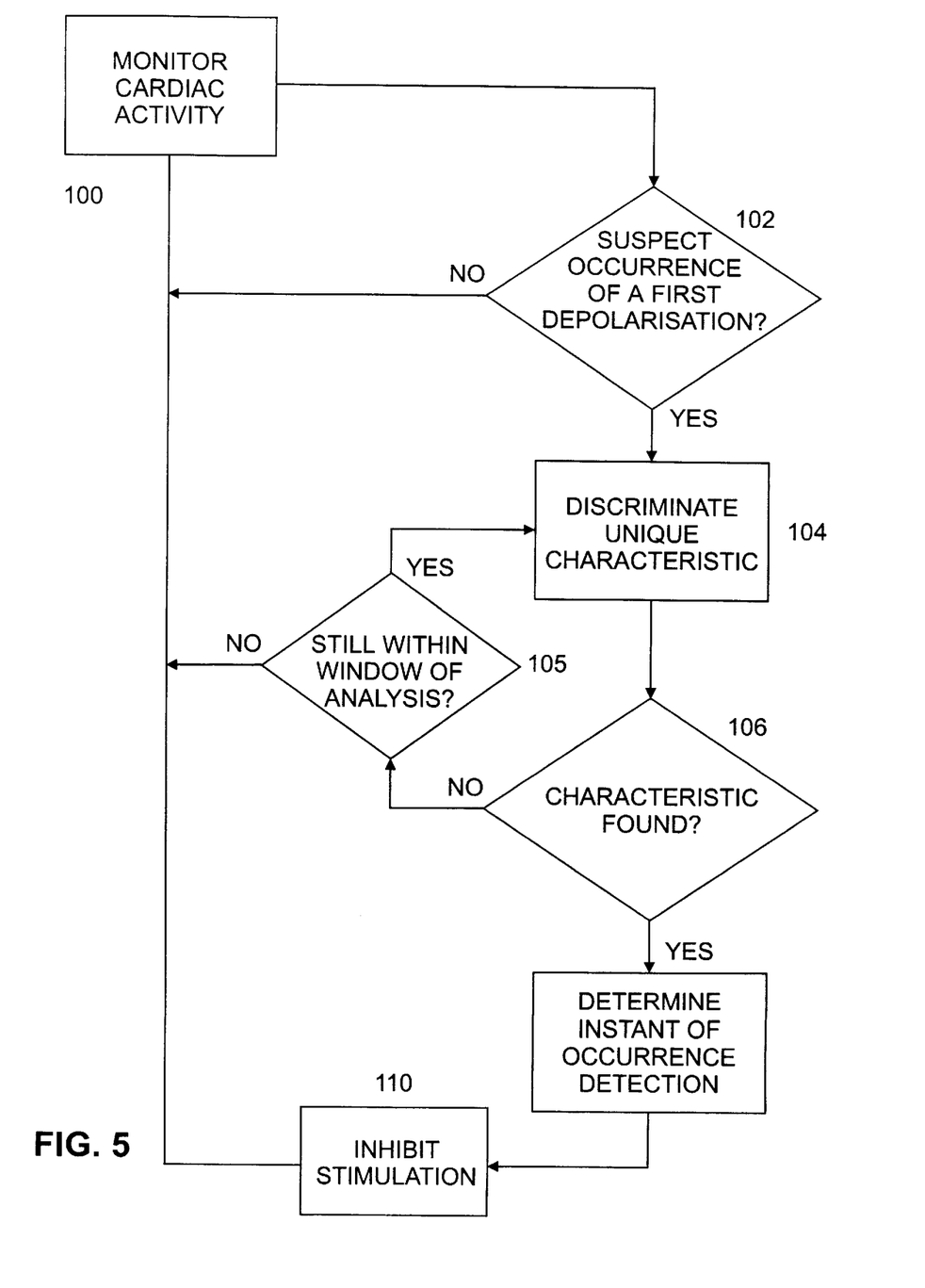
FIG. 5 illustrates a flow chart of an examplary sequence of operations implementable in the device of FIG. 4.

For a software controlled implantable medical device, one useful sequence of operations according to one embodiment of the method of the present invention is illustrated in FIG. 5 as follows.

Cardiac activity is monitored. (step 100). Based on the monitored signals, a determination is made whether a first spontaneous depolarisation has occurred. (step 102). When a first spontaneuos depolarisation is detected, a unique charactersitic of the signal is discriminated. (step 104). If this characteristic is found (step 106), stimulation is inhibited. (step 110). If not, a determination is made whether still within the window of analysis. (step 105). If within the window of analysis, discrimination (step 104) continues. If, on the otherhand, the window has expired (i.e., no longer within the window of analysis), the sequence process begins anew with cardiac activity monitoring (step 100).

This illustrative sequence will run in a continuous loop during expected operation.

Variations in or modifications to this logic sequence, which is presented for purposes of non-limiting illustration, will, of course, be understood by one of ordinary skill in the art. For example, in step 110, in conjunction with or in lieu of inhibiting stimulation, rhythym stability or other calculations may be performed.

One additional advantage of the present invention is that, because it need not require additional circuitry, a software routine to implement the present invention may be downloaded using telemetry by conventionl circuits to an already implanted device to enable the implanted device to be configured to perform the present invention.

The present invention has been described with reference to specific embodiments thereof. It will be understood by one skilled in the art that these are not exclusive embodiments, and while the foregoing description of illustrative embodiments discusses many specificities, these enabling details should not be construed as limiting the scope of the invention, and it will be readily understood by those persons skilled in the art that the present invention is susceptible to many modifications, adaptations, and equivalent implementations without departing from this scope and without diminishing its advantages.

We claim:

1. An active implantable medical device comprising:
   means for collecting a cardiac signal corresponding to a spontaneous myocardium activity;
   means for processing said collected cardiac signal and determining therefrom an information corresponding to an occurrence of a spontaneous myocardium depolarization;
   means, responsive to said processing means determining said information, for analyzing said collected cardiac signal and determining a unique characteristic of said collected signal, said unique characteristic having a temporal information representative of a time of occurrence of said depolarization.

2. The device of claim 1, wherein the analyzing means further comprises means for discriminating a peak of auto-correlation in the collected cardiac signal, wherein said time of occurrence is based on said auto-correlation peak.

3. The device of claim 1, wherein the analyzing means further comprises means for identifying a unique singularity in the collected cardiac signal, said unique singularity having a time of occurrence, wherein said temporal information is the time of occurrence of said unique singularity.

4. The device of claim 1, wherein the analyzing means further comprises means for identifying an extreme value of the first derivative of the collected cardiac signal, said extreme value having a time of occurrence, wherein said temporal information is the time of occurrence of said extreme value.

5. The device of claim 4, wherein the analyzing means further comprises means for identifying an extreme negative value of the first derivative of the collected cardiac signal, wherein said temporal information is the time of occurrence of said extreme negative value.

6. The device of claim 1, wherein the analyzing means further comprises means for identifying a maximum amplitude of the collected cardiac signal, said maximum amplitude having a time of occurrence, wherein said temporal information is the time of occurrence of said maximum amplitude.

7. The device of claim 1, wherein said analyzing means further comprises means for analyzing said collected cardiac signal during a time window.

8. The device of claim 7, wherein said analyzing means further comprises means for initiating said time window at the detected occurrence of said spontaneous myocardium depolarization.

9. The device of claim 7, wherein said analyzing means further comprises means for initiating said time window a period preceding the detected occurrence of said spontaneous myocardium depolarization.

* * * * *

UNITED STATES PATENT AND TRADEMARK OFFICE
CERTIFICATE OF CORRECTION

PATENT NO. : 6,149,601
DATED : November 21, 2000
INVENTOR(S) : Jean-Luc Bonnet and Remi Nitzsche It is certified that error appears in the above-identified patent and that said Letters Patent is hereby corrected as shown below:

Title page,
Item [56], References Cited, OTHER PUBLICATIONS, "M. Kirhner et al.," reference, after "interval" delete "measruement" and insert -- measurement --; after "computers" delete "In cardiology and insert -- in Cardiology --;

Column 1,
Line 29, after "or" delete ","
Lines 64-65, after "interval" delete "," and insert -- ; -- and after "otherwise" insert -- , --.

Column 2,
Line 2, after "energy, and" insert -- , --;
Line 20, after "regard" delete "of" and insert -- to --;
Line 33, after "non" insert -- - --;

Column 3,
Line 51, after "present" delete "invention"; and" and insert -- invention; and --;

Column 4,
Line 11, after "say" insert -- , --;
Line 19, after "and" insert -- , --;
Line 27, before "Fig." delete "the"
Line 31, before "therefore" insert -- , --;
Line 35, after "In" delete "others" and insert -- other --
Line 64, before "Fig. 1" delete "the";
Line 67, before "Fig. 2" delete "the"

Column 5,
Lines 11-12, after "window of" delete "analysis" and insert -- analysis, --
Line 42, after "(d)" insert -- , --; after "stability" delete "charactersistics" and insert -- characteristics --; and after "(b)" insert -- , --

UNITED STATES PATENT AND TRADEMARK OFFICE
CERTIFICATE OF CORRECTION

PATENT NO.    : 6,149,601
DATED         : November 21, 2000
INVENTOR(S)   : Jean-Luc Bonnet and Remi Nitzsche It is certified that error appears in the above-identified patent and that said Letters Patent is hereby corrected as shown below:

Column 6,
Line 1, after "say" insert ",";
Line 11, after "two" insert -- analysis --; and after "windows" delete "of analysis"
Lines 50 and 51-52, after "discriminated" and "inhibited" respectively: delete "."
Lines 46 and 48, after "monitored" and "occurred" respectively, delete "."
Lines 53 and 55, after "analysis" delete "."; after "on the" delete "otherhand" and insert -- other hand --
Lines 49-50, before "depolarisation" delete "spontaneuos" and insert -- spontaneous -- and after "unique" delete "charactersitic" and insert -- characteristic --
Line 64, after "stimulation" delete "rhythym" and insert -- rhythm --

Column 7,
Line 2, before "circuits" delete "conventionl" and insert -- conventional --

Column 8,
Line 31, after "window" insert -- at --;

Signed and Sealed this

Fifth Day of October, 2004

JON W. DUDAS
*Director of the United States Patent and Trademark Office*